(12) United States Patent
Anderson et al.

(10) Patent No.: US 7,798,368 B2
(45) Date of Patent: Sep. 21, 2010

(54) FLUID DISPENSING DEVICE

(75) Inventors: Gregor John McLennan Anderson, Ware (GB); Michael Birsha Davies, Ware (GB); Paul Kenneth Rand, Ware (GB)

(73) Assignee: Glaxo Group Limited, Greenford, Middlesex (GB)

( * ) Notice: Subject to any disclaimer, the term of this patent is extended or adjusted under 35 U.S.C. 154(b) by 1035 days.

(21) Appl. No.: 10/513,200

(22) PCT Filed: May 7, 2003

(86) PCT No.: PCT/EP03/04857

§ 371 (c)(1),
(2), (4) Date: Nov. 2, 2004

(87) PCT Pub. No.: WO03/095006

PCT Pub. Date: Nov. 20, 2003

(65) Prior Publication Data

US 2005/0211241 A1      Sep. 29, 2005

(30) Foreign Application Priority Data

May 9, 2002   (GB) ................. 0210605.2

(51) Int. Cl.
*B67D 7/84* (2010.01)
*A61M 11/00* (2006.01)

(52) U.S. Cl. .............. 222/162; 222/183; 128/200.23; 128/203.14; 604/412

(58) Field of Classification Search .......... 222/160, 222/162, 556, 183; 128/200.23, 203.14, 128/206.11, 200.14, 200.22, 207.18; 604/412, 604/414
See application file for complete search history.

(56) References Cited

U.S. PATENT DOCUMENTS

| 2,568,286 | A | * | 9/1951 | Littlefield ............... 222/103 |
| 3,272,391 | A | * | 9/1966 | Meshberg ............... 222/162 |
| 4,083,476 | A |   | 4/1978 | Schwartz et al. |
| 5,062,549 | A |   | 11/1991 | Smith et al. |
| 5,529,219 | A | * | 6/1996 | Ward ...................... 222/156 |
| 5,899,365 | A |   | 5/1999 | Hochrainer et al. |
| 6,189,739 | B1 |  | 2/2001 | Von Schuckmann |

(Continued)

FOREIGN PATENT DOCUMENTS

DE       19610456       9/1997

(Continued)

OTHER PUBLICATIONS

Patent Abstracts of Japan, 1997(06):JP09048455 (Feb. 18, 1997).

*Primary Examiner*—Kevin P Shaver
*Assistant Examiner*—Stephanie E Tyler
(74) *Attorney, Agent, or Firm*—James P. Riek

(57) ABSTRACT

A fluid dispenser (5, 105) is disclosed having a housing (9, 109) and a pump action fluid discharge device (8, 108). The pump action fluid discharge device (8, 108) is arranged to be actuated by a pair of opposing levers (20, 21); (120, 121) which are pivotally connected to part of the housing (9, 109). When the levers (20, 21); (120, 121) are squeezed together the fluid discharge device (8, 108) is urged towards a nozzle (11, 111) causing a single dose of fluid to be dispensed from the nozzle (11, 111).

48 Claims, 8 Drawing Sheets

U.S. PATENT DOCUMENTS

| | | | |
|---|---|---|---|
| 6,315,165 B1 * | 11/2001 | Regan | 222/103 |
| 6,527,144 B2 * | 3/2003 | Ritsche et al. | 222/162 |
| 6,745,760 B2 * | 6/2004 | Grychowski et al. | 128/200.14 |
| 6,792,941 B2 * | 9/2004 | Andersson | 128/200.23 |
| 7,353,971 B2 * | 4/2008 | Stradella | 222/162 |
| 2002/0011530 A1 | 1/2002 | Fuchs | |
| 2004/0220004 A1 | 11/2004 | Bourc'his | |

FOREIGN PATENT DOCUMENTS

| | | | |
|---|---|---|---|
| EP | 0111875 A1 | 6/1984 | |
| FR | 1444387 | 7/1966 | |
| FR | 2807954 | 10/2001 | |
| FR | 2812826 | 2/2002 | |
| FR | 2830519 | 4/2003 | |
| GB | 659132 | 10/1951 | |
| GB | 1097254 | 1/1968 | |
| GB | 2251898 | 7/1992 | |
| JP | 200085867 A | 3/2000 | |
| WO | 9405593 A1 | 3/1994 | |
| WO | WO 00/07740 | 2/2000 | |
| WO | WO 00/00405 * | 6/2000 | 222/103 |
| WO | WO 02/20370 | 3/2002 | |
| WO | WO 03/002892 | 1/2003 | |
| WO | WO 03/029105 | 4/2003 | |

* cited by examiner

FLUID DISPENSING DEVICE

CROSS-REFERENCE TO RELATED APPLICATIONS

This application is filed under 35 U.S.C. §371 as the United States National Phase Application of International Application No. PCT/EP03/04857 filed May 7, 2003, which claims priority to GB Application No. 02110605.2 filed May 9, 2002.

The present invention relates to a medicament dispenser and in particular to fluid dispensing device for use as a nasal inhaler.

It is well known to provide a medicament dispenser in which fluid is dispensed via a nozzle or orifice upon the application of a force by a user to an actuation lever or button. Such devices may be arranged to dispense a single dose or may alternatively be arranged with a reservoir containing several doses to be dispensed. An example of such a pump action spray is shown and described in U.S. Pat. No. 4,771,769.

It is a problem with such a prior art spray that because only one finger actuated member is used to causing spraying some of the applied force is wasted. this is because the reaction force applied to the device to counteract the force applied to the finger actuated member is used merely to hold the dispenser stable and is not utilised for pumping fluid.

It is an object of this invention to provide a fluid dispensing device that is easier to use and in particular a device which provides a more efficient dispensing of fluid.

According to a first aspect of the invention there is provided a fluid dispensing device for spraying a fluid into a body cavity comprising a housing, a nozzle for insertion into a body cavity, a fluid discharge device moveably housed within the housing, the fluid discharge device comprising a container for storing the fluid to be dispensed and a compression pump having a suction inlet located within the container and a discharge outlet for transferring fluid from the pump to the nozzle and finger operable means to apply a force to the container to move the container towards the nozzle so as to actuate the pump wherein the finger operable means comprises of two opposing levers each of which is pivotally connected to part of the housing and is arranged to act upon the container so as to urge the container towards the nozzle when the two levers are squeezed together by a user.

The two levers may act upon a base portion of the container.

Advantageously the fluid dispensing device may include a pre-load means which prevents movement of the two levers until more than a pre-determined force has been applied to the levers.

The fluid discharge device may have a longitudinal axis and each of the levers may have an abutment surface arranged at an angle to the longitudinal axis of the fluid discharge device for abutment against a base portion of the container so as to convert a force applied to the levers substantially transversely to the longitudinal axis of the fluid discharge device into a force along the longitudinal axis of the fluid discharge device.

The nozzle may have a longitudinal axis and the longitudinal axis of the fluid discharge device may be aligned with the longitudinal axis of the nozzle.

The fluid discharge device may have a longitudinal axis and at least part of the surface of a base portion of the container may be inclined at an angle with respect to the longitudinal axis of the fluid discharge device so as to form an inclined surface, the or each inclined surface being arranged to be acted upon by the levers so as to convert a force applied to the levers substantially transversely to the longitudinal axis of the fluid discharge device into a force along the longitudinal axis of the fluid discharge device.

The inclined surface of the base portion of the container may be a conical surface, a frusto-conical surface or a spherically shaped surface.

Alternatively, the base portion of the container may have two inclined surfaces each arranged for co-operation with a respective one of the levers.

The container may have two or more supports to allow the container to be stood up on the base portion.

In accordance with one embodiment of the first aspect of the invention the housing and the nozzle are made as a single a plastic component.

Each of the levers may be pivotally connected to part of the housing by a respective living hinge.

The housing may have a front wall, a rear wall and two opposing side walls and each of the levers is pivotally connected to a respective one of the two side walls by a living hinge.

At least one of the front wall and the rear wall may have an aperture therein to view the level of the fluid in the container.

There may be apertures in the front and rear walls to view the level of the fluid in the container.

The discharge outlet from the pump may be a tubular delivery tube and a tubular guide may be formed within the nozzle to align and locate the delivery tube correctly with respect to the nozzle.

According to a further embodiment of the first aspect of the invention the housing comprises of a plastic cover member and a plastic body member.

The fluid dispensing device may include a means to prevent inadvertent movement of the two levers when not in use.

The means may be a portion of the cover member which overlies an end portion of each lever.

The nozzle may be formed as an integral part of the body member.

At least a part of the nozzle may be moulded from a soft-touch plastics material. The body member may be fastened within the cover member so that the nozzle projects from one end of the cover member.

Each of the levers may be pivotally connected to the body member.

Preferably, each of the levers may be pivotally connected to the body member by a living hinge.

Alternatively, each of the levers may be pivotally connected to the cover member. The discharge outlet from the pump may be a tubular delivery tube and a tubular guide may be formed within the body member to align and locate the delivery tube correctly with respect to the nozzle.

The cover member may comprise of two cover shells joined together at one end by an annular ring.

The body member may be engaged with the annular ring to fasten the cover member to the body member.

There may be a snap connection between the annular ring and part of the body member to fasten the body and cover members together.

Each of the cover shells may have an aperture formed therein from which, in use, a part of a respective one of the levers projects.

The part of each lever which projects from the aperture may be a ribbed finger grip. A part of each lever may be moulded from a soft-touch plastics material.

Preferably, the part of each lever may be moulded from a soft-touch plastics material is the ribbed finger grip.

At least one longitudinal edge of each cover shell may have a recess formed therein and the recesses may co-operate to define a window through which the level of the fluid in the container can be checked.

Preferably, both longitudinal edges of each cover shell may have a recess formed therein and the recesses may co-operate to define two windows on opposite sides of the housing through which the level of the fluid in the container can be checked.

A protective end cap for the nozzle may be connected to the annular ring.

The protective end cap may be arranged to be biased to a closed position or may alternatively be biased to an open position.

The end cap, the annular ring and the two cover shells may be made as a one piece plastic component.

According to a second aspect of the invention there is provided a fluid discharge device for use in a fluid dispensing device in accordance with the first aspect of the invention wherein the fluid discharging device comprises of a container for storing a fluid to be dispensed and a compression pump attached to one end of the container, the pump having a suction inlet located within the container and a discharge outlet for transferring, in use, fluid from the pump to a nozzle wherein the fluid discharge device has a longitudinal axis and the container has a base portion at least part of which is inclined at an angle with respect to the longitudinal axis of the fluid discharge device.

The inclined surface of the base portion of the container may be a conical surface, a frusto-conical surface or a spherical surface.

Alternatively, the base portion of the container may have two opposing inclined surfaces.

The container may have two or more supports to allow the container to be stood up on the base portion.

According to a third aspect of the invention there is provided a housing assembly for a fluid discharge device, the housing assembly comprising a housing for moveably supporting the discharge device, a nozzle extending from the housing for insertion into a body cavity and finger operable means to apply, in use, a force to the fluid discharging device wherein the finger operable means comprises of two opposing levers to apply, in use, a force to the fluid discharging device so as to actuate the fluid discharge device and supply fluid to the nozzle.

According to one embodiment of the third aspect of the invention the housing and the nozzle are made as a single a plastic component.

The levers may be pivotally connected to part of the housing.

Preferably, each of the levers may be pivotally connected to part of the housing by a living hinge.

According to a further embodiment of the third aspect of the invention the housing comprises of a plastic cover member and a plastic body member and the nozzle is formed as an integral part of the body member.

The body member may be fastened within the cover member so that the nozzle projects from one end of the cover member.

Each of the levers may be pivotally connected to the body member.

Preferably, each of the levers may be pivotally connected to the body member by a living hinge.

Alternatively, each of the levers may be pivotally connected to the cover member. A tubular guide may be formed within the body member to align and locate, in use, a delivery tube of the fluid discharge device correctly with respect to the nozzle.

The cover member may comprise of two cover shells joined together at one end by an annular ring.

The body member may be engaged with the annular ring to fasten the cover member to the body member.

Each of the cover shells may have an aperture formed therein from which, in use, a part of a respective one of the levers projects.

The part of each lever which projects from the aperture may be a ribbed finger grip.

At least one longitudinal edge of each cover shell may have a recess formed therein and the recesses may co-operate to define a window through which the level of the fluid in the container can be checked.

Both longitudinal edges of each cover shell may have a recess formed therein and the recesses may co-operate to define two windows on opposite sides of the housing through which the level of the fluid in the container can be checked.

A protective end cap for the nozzle may be connected to the annular ring.

The end cap, the annular ring and the two cover shells may be made as a one piece plastic component.

Each of the levers may have an inclined abutment surface for abutment, in use, against the fluid discharge device so as to convert a force applied to the levers substantially transversely to a longitudinal axis of the fluid discharge device into a force along the longitudinal axis of the fluid discharge device.

The invention will now be described further with reference to the accompanying drawing in which:—

Figure 1:
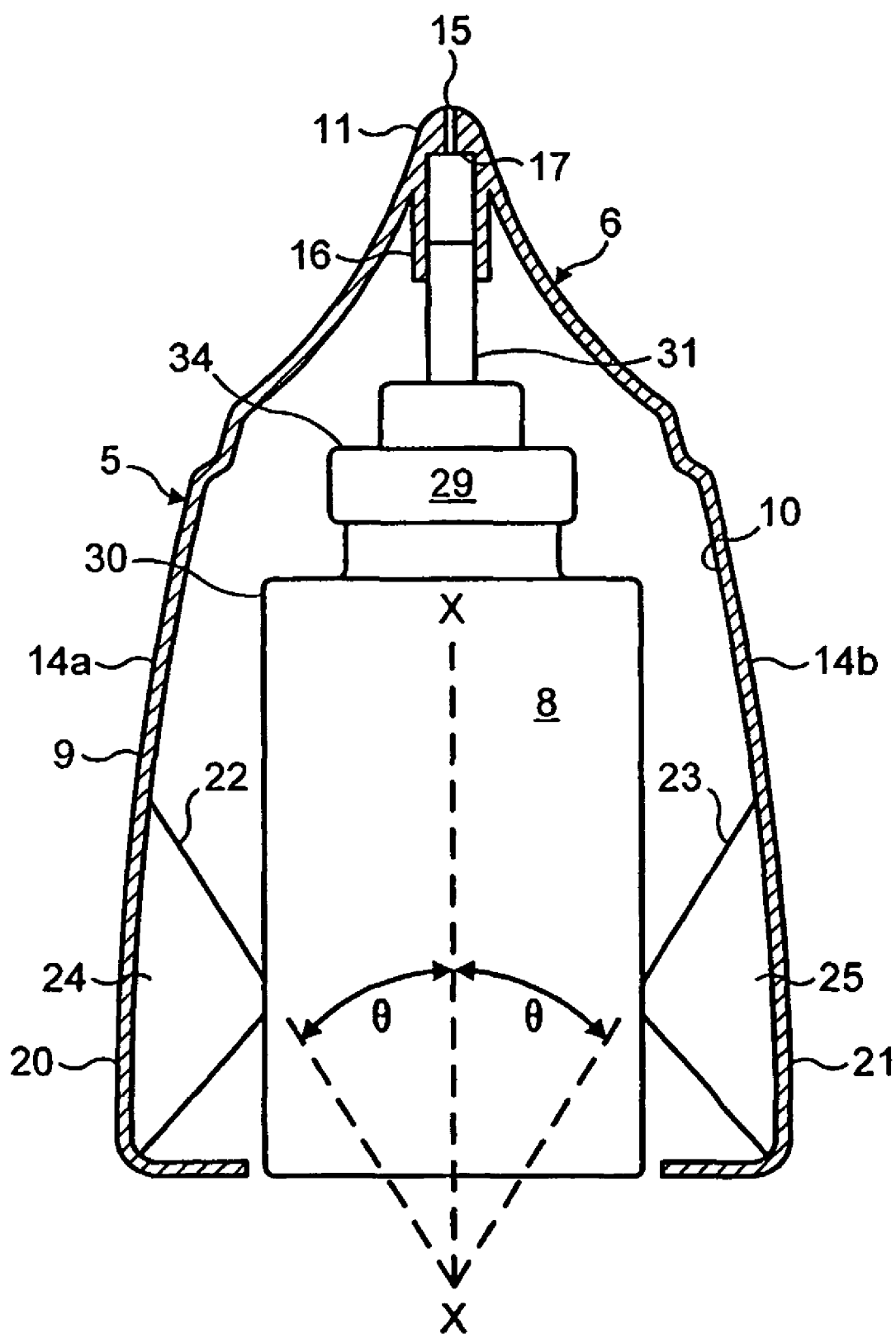
FIG. 1 is a cross-section through a first embodiment of a fluid dispensing device according to the invention in a ready for use state.
Figure 2:
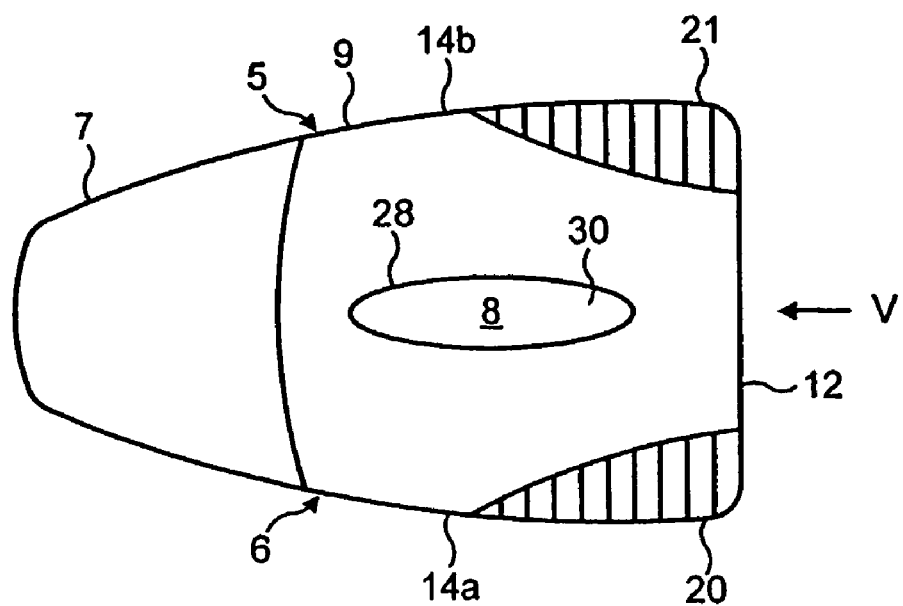
FIG. 2 is a front view of the fluid dispensing device shown in FIG. 1 in a closed or stored condition with the fluid dispensing device laid on one side.
Figure 3:
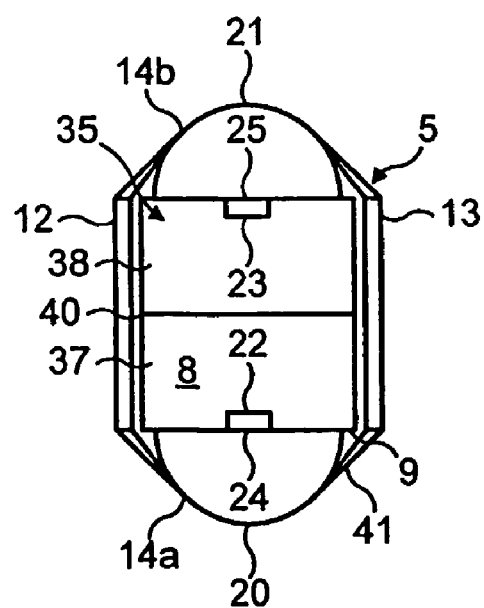
FIG. 3 is an end view of the fluid dispensing device shown in FIG. 2 in the direction of arrow 'V' on FIG. 2.

With reference to FIGS. 1 to 5 there is shown a first embodiment of a fluid dispensing device 5 for spraying a fluid into a body cavity comprising a housing 9, a nozzle 11 for insertion into a body cavity, a fluid discharge device 8 moveably housed within the housing 9, the fluid discharge device 9 comprising a container 30 for storing the fluid to be dispensed and a compression pump 29 having a suction inlet 32 located within the container 30 and a discharge outlet 31 for transferring fluid from the pump 29 to the nozzle 11 and finger operable means 20, 21 to apply a force to the container 30 to move the container 30 towards the nozzle 11 so as to actuate the pump 29. The finger operable means being in the form of two opposing levers 20, 21 each of which is pivotally connected to part of the housing 9 and is arranged to act upon a base portion 35 of the container 30 so as to urge the container 30 towards the nozzle 11 when the two levers 20, 21 are squeezed together by a user.

In more detail the fluid dispensing device 5 comprises of a plastic moulded body 6 and the fluid discharge device 8 and further comprises of a protective end cap 7 having an inner surface for engagement with the body 6 to protect the dispensing nozzle 11.

The body 6 is made from a plastic material such as polypropylene and defines a housing 9 and a dispensing nozzle 11 so that the housing 9 and the nozzle 11 are made as a single plastic component.

The housing 9 defines a cavity 10 formed by a front wall 12, a rear wall 13 and first and second end walls 14a, 14b. The dispensing nozzle 11 is connected to one end of the housing 9, extends away from the housing 9 and has an external tapering form. It will be appreciated that the shape of the housing need not be oval it could be cylindrical or any other convenient shape.

At least one of the front wall 12 and the rear wall 13 has an aperture 28 therein to view the level of the fluid in the container 30 and in the embodiment shown there are apertures 28 in the front and rear walls 12, and 13 to view the level of the fluid in the container 30.

The discharge outlet from the pump 29 is in the form of a tubular delivery tube 31 and a tubular guide in the form of an outlet tube 16 is formed within the nozzle 11 to align and locate the delivery tube 31 correctly with respect to the nozzle 11.

An annular abutment 17 is formed at the end of the outlet tube 16. The annular abutment 17 defines the entry to an orifice 15 through which fluid can flow in use and is arranged for abutment with an end of the delivery tube 31.

The fluid discharge device 8 has a longitudinal axis X-X and each of the levers 20, 21 has an abutment surface 22, 23 arranged at an angle θ to the longitudinal axis X-X of the fluid discharge device 8 for abutment against a base portion 35 of the container so as to convert a force applied to the levers 20, 21 substantially transversely to the longitudinal axis X-X of the fluid discharge device 8 into a force along the longitudinal axis X-X of the fluid discharge device 8.

This arrangement allows a standard fluid discharge device to be used without modification.

The nozzle 11 has a longitudinal axis Y-Y and the longitudinal axis X-X of the fluid discharge device 8 is aligned with the longitudinal axis Y-Y of the nozzle 11. This has the advantage that when the pump 29 is actuated the force applied to the tubular delivery tube 31 is along the axis of the tubular delivery tube and no bending or deflection of the delivery tube 31 will occur due to the applied force.

At least part of the surface of the base portion 35 of the container 30 is inclined at an angle φ with respect to the longitudinal axis X-X of the fluid discharge device 8 so as to form an inclined surface, the or each inclined surface being arranged to be acted upon by the levers 20, 21 so as to convert a force applied to the levers 20, 21 substantially transversely to the longitudinal axis X-X of the fluid discharge device 8 into a force along the longitudinal axis X-X of the fluid discharge device 8.

Although in the disclosed embodiment both the levers and the container have surfaces inclined to the longitudinal axis of the fluid discharge device and that in the disclosed embodiment the angle θ is approximately equal to the angle φ this need not be the case. Only the container or the levers need have an inclined surface or some other arrangement to apply the force from the levers to the container could be used.

The base portion 35 of the container 30 has two inclined surfaces 37, 38 each arranged for co-operation with a respective one of the levers 20, 21.

However it will be appreciated that the inclined surface of the base portion of the container could be a conical, frusto-conical or part spherical surface.

The inclined surface 37 is arranged to co-operate with the abutment surface 22 and the inclined surface 38 is arranged to co-operate with the abutment surface 23.

The abutment surface 22 is formed by an edge of a web 24 formed as part of the lever 20 and the abutment surface 23 is formed by an edge of a web 25 formed as part of the lever 21.

A pre-loading means in the form of small ridge (not shown) is formed near to the end of each abutment surface 22, 23. In the ready for use position this lies against a side of the container 30 at the juncture of the side of the container with the base portion 35. The purpose of this ridge is to prevent the levers 20, 21 from moving the container 30 until more than a pre-determined load has been applied to the levers 20, 21. Once this pre-determined load is exceeded the pressure being applied to the levers is such that the container is very rapidly moved towards the nozzle 11. This prevents the levers 20, 21 being slowly squeezed together which will not produce a uniform spray and if done very slowly will merely cause the fluid to dribble out of the nozzle 11. However it will be appreciated that many alternative mechanisms could be employed to produce this pre-load effect and that the pump itself could be provided with such a device that needs to be overcome.

Each of the levers 20, 21 is pivotally connected to part of the housing 9 by a respective living hinge. In the embodiment shown each of the levers 20, 21 is pivotally connected to a respective one of the two side walls 14a, 14b by a respective living hinge 26, 27.

The fluid discharge device 8 is in most respects conventional and will only be described briefly herein.

The fluid discharge device 8 has a hollow container 30 defining a reservoir containing several doses of the fluid to be dispensed and a compression pump 29 attached to one end of the container 30.

The container 30 as shown is made from a translucent or transparent plastics material however it will be appreciate that it could be made from other translucent or transparent materials such as glass.

The container has two or more supports to allow the container to be stood up on the base portion 35 and as shown two supports 40, 41 are moulded as an integral part of the container 30. These supports are useful in that, because the base portion 35 is made up of two inclined surfaces 37, 38, it could not normally be stood up vertically. The pump 29 includes a plunger (not shown) slidingly engaged within a pump casing 34 which defines a chamber (not shown) sized to accommodate a single dose of fluid. The plunger is attached to the tubular delivery tube 31 which is arranged to extend from one end of the pump 29 for co-operation with the outlet tube 16 of the dispensing nozzle 11. The plunger includes a piston (not shown) slidably supported in the chamber formed in the pump casing 34.

The fluid is discharged through a discharge channel defined by the tubular delivery tube 31 into the orifice 15 of the dispensing nozzle 11.

The size of chamber is such that it accommodates a single dose of fluid, the diameter of the chamber and piston combined with the stroke of the plunger being such that a full stroke of the plunger in the chamber will produce a change in volume equal to a single dose of fluid.

The pump casing 34 is connected to the container 30 such that when the piston is moved by a return spring (not shown) into a start position a new dose of fluid is drawn into the cylinder via the suction inlet in the form of a pick-up tube 32 from the container 30 ready for discharge.

The tapering form of the base portion 35 of the container 30 is advantageous in that it allows the pick up tube 32 to collect, without special orientation of the container, more fluid than if a flat bottomed container is used.

The end cap 7 is a tubular component which is closed at one end and has a thin flexible side wall which defines a cavity into which the nozzle 11 is engaged to protect the nozzle 11 from damage.

It is envisaged that the end cap may be attached to the body by a flexible strap or tether which could be moulded as part of the end cap or the end cap and the body could be made as a single component.

Assembly and operation of the fluid dispensing device is as follows.

Figure 4:
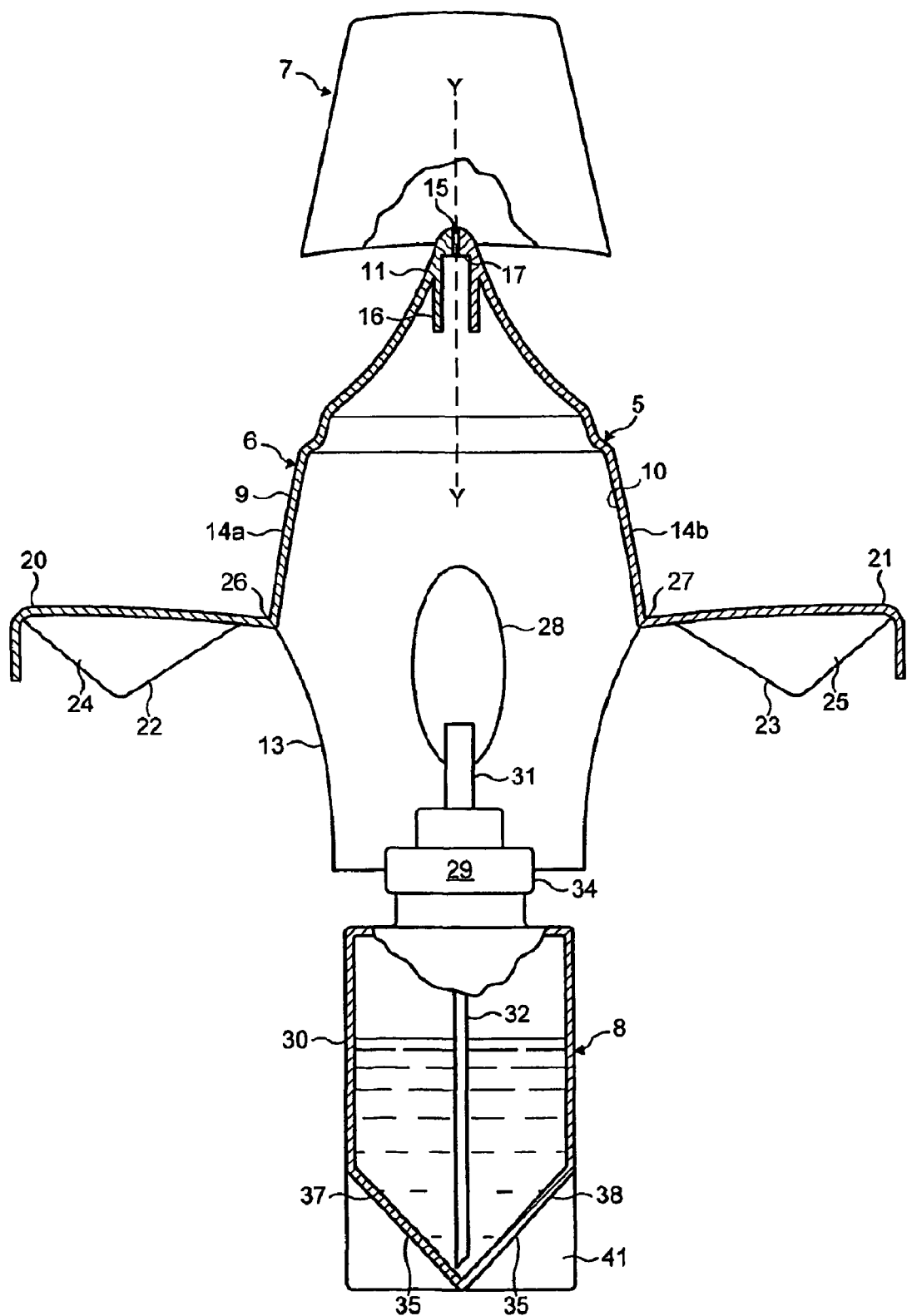
FIG. 4 is a cross-section similar to that shown in FIG. 1 but showing the insertion of a fluid discharge device according to a second aspect of the invention into a housing assembly according to a third aspect of the invention.

FIG. 4 shows the fluid dispensing device 5 in a partly assembled state in which the two levers 20, 21 have been moved into a loading position to allow the fluid discharge device 8 to be inserted into the cavity 10 in the housing 9.

From the position shown the fluid discharge device 8 is moved upwardly until the delivery tube 31 fully engages with the outlet tube 16. The two levers 20, 21 are then folded down into the position shown in FIG. 1 such that end portions of the abutment surfaces 22, 23 abut gently against the inclined surfaces 37, 38 of the container 30. The levers 20, 21 in this position are used to hold the fluid discharge device 8 within the housing 9.

If required the container 30 or the pump casing 34 could be slidably engageable with one or more support structures (not shown) to assist with the location and retention of the fluid discharge device 8 in the housing 9.

Figure 5:
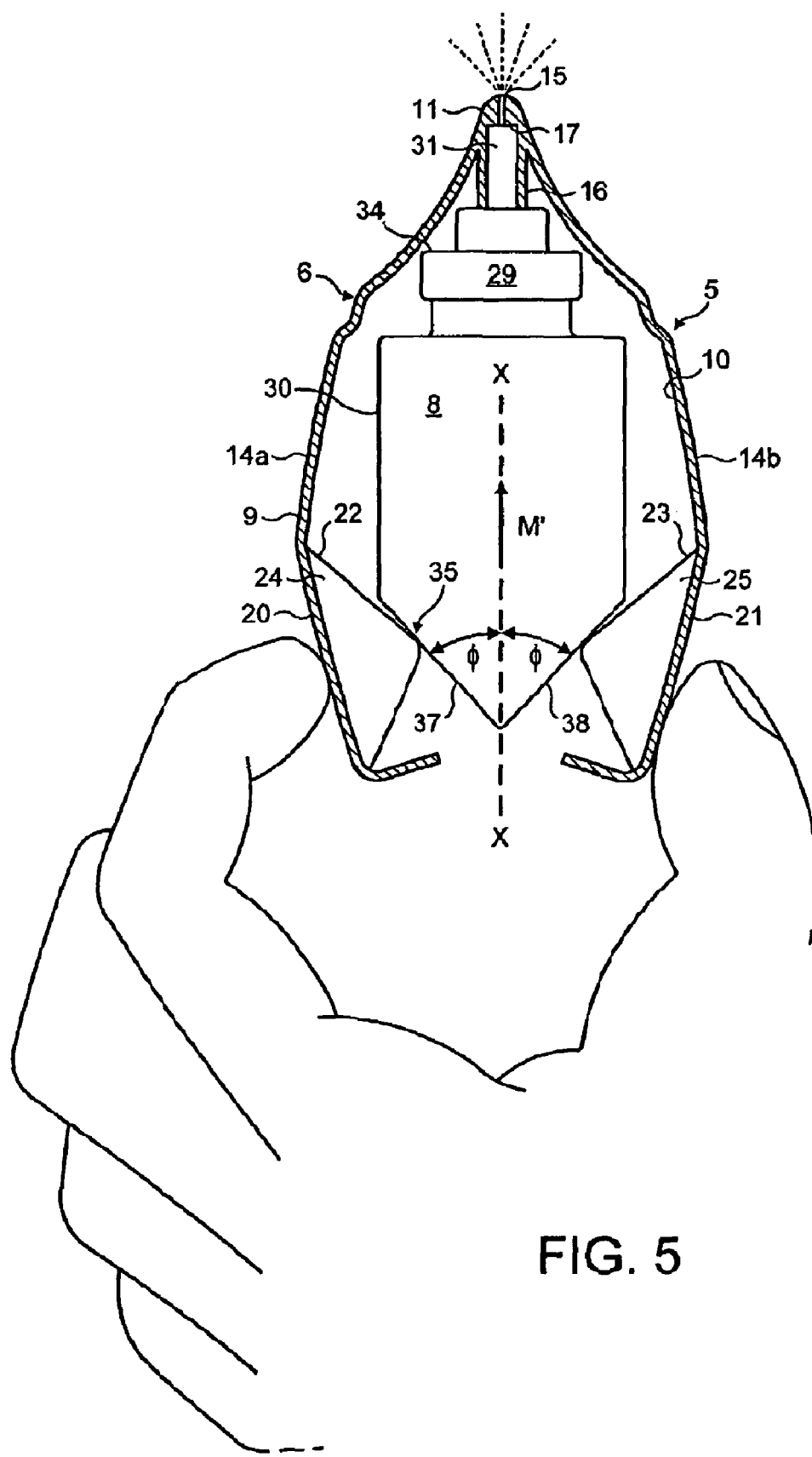
FIG. 5 is a cross-section similar to that of FIG. 1 but showing the fluid dispensing device in use.

As shown in FIG. 5, a user first grasps the fluid dispensing device 5 by the two levers 20, 21. Provided that only a light pressure is applied to the levers 20, 21 no fluid will be discharged and the user is able to manoeuvre the dispensing nozzle 11 of the fluid dispensing device 5 into the body orifice into which fluid is required to be dispensed. This is because of the presence of the pre-loading means.

If the user then squeezes the two levers 20, 21 together with increasing force the pre-determined load of the pre-loading means will eventually be overcome and the interaction of the abutment surfaces 22, 23 with the inclined surfaces 37, 38 will then cause the container 30 to be moved rapidly towards the nozzle 11 as indicated by the arrow 'M' on FIG. 5.

However, the abutment between the end of the delivery tube 31 and the annular abutment 17 will prevent movement of the delivery tube 31 in the same direction. This effect of this is to cause the delivery tube 31 to push the plunger into the pump casing 34 thereby moving the piston of the pump in the cylinder. This movement causes fluid to be expelled from the cylinder into the delivery tube 31. The fluid forced into the delivery tube is then transferred into the orifice 15 from where it is expelled as a fine spray into the body orifice.

Upon releasing the pressure applied to the levers 20, 21 the delivery tube 31 is urged out of the pump casing by the internal return spring and causes fluid to be drawn up the pick-up tube 32 to re-fill the cylinder.

The actuating procedure can then be repeated until all of the fluid in the container has been used. However, only one or two doses of fluid are normally administered at a time.

When the container is empty a new fluid discharge device 8 is loaded into the housing 9 thereby restoring the fluid dispensing device 5 into a useable condition.

With reference to FIGS. 6 to 11 there is shown a second embodiment of a fluid dispensing device for spraying a fluid into a body cavity which is in many respects similar to that previously described.

The fluid dispensing device 105 comprising a housing 109, a nozzle 111 for insertion into a body cavity, a fluid discharge device 108 moveably housed within the housing 109, the fluid discharge device 108 comprising a container 130 for storing the fluid to be dispensed and a compression pump 129 having a suction inlet located within the container 130 and a discharge outlet for transferring fluid from the pump 129 to the nozzle 111 and finger operable means 120, 121 to apply a force to the container 130 to move the container 130 towards the nozzle 111 so as to actuate the pump 129. The finger operable means is in the form of two opposing levers 120, 121 each of which is pivotally connected to part of the housing 109 and is arranged to act upon the container 130 so as to urge the container 130 towards the nozzle 111 when the two levers 120, 121 are squeezed together by a user.

In more detail, the housing 109 comprises of a plastic cover member 110 and a plastic body member 106 both of which are moulded from a suitable plastic material such as polypropylene. It will be appreciated that the shape of the housing need not be oval it could be cylindrical or any other convenient shape.

The nozzle 111 is formed as an integral part of the body member 106 and the body member 106 is fastened within the cover member 110 so that the nozzle 111 projects from one end of the cover member 110. The outer surface or a part of the outer surface of the nozzle could be made from a soft-touch plastics material.

The cover member 110 comprises of two cover shells 118a, 118b joined together at one end by an annular ring 119.

A protective end cap 107 for the nozzle 111 is connected to the annular ring 119 such that the end cap 107, the annular ring 119 and the two cover shells 118a, 118b are made as a one piece plastic component. The protective end cap may be moulded and arranged so as to be biased to a closed position or may alternatively be biased to an open position.

The protective end cap 107 has an inner surface for engagement with the body 106 to protect the dispensing nozzle 111. Two detents 149 are provided on the inner surface of the end cap 107 to releasably hold the end cap 107 in place when it is in its protective position. The end cap 107 has a tubular sealing means 140 which is arranged for engagement with a recess 141 in the end of the nozzle 111 so as to prevent leakage from the nozzle 111 when the end cap 107 is in place.

Each of the cover shells 118a and 118b is of a semi-cylindrical shape and has two longitudinal edges 112, an end edge 113 and two transverse edges 116. At least one longitudinal edge 112 of each cover shell 118a, 118b has a recess 114 formed therein. The recesses 114 co-operate to define a window 150 through which the level of the fluid in the container 130 can be checked.

In the embodiment shown and described both longitudinal edges 112 of each cover shell 118a, 118b have a recess 114 formed therein and the recesses 114 co-operate to define two windows 150 on opposite sides of the housing 109 through which the level of the fluid in the container 130 can be checked.

Each of the cover shells 118a, 118b has an aperture 145a, 145b formed therein from which, in use, a part of a respective one of the levers 120, 121 projects. The part of each lever 120, 121 which projects from the aperture 145a, 145b is a ribbed finger grip 146 formed at the opposite end of each lever 120, 121 from where it is hingedly connected to the body member 106. A part of each lever and in particular the finger grips may be moulded from a soft touch plastic material.

Figure 7:
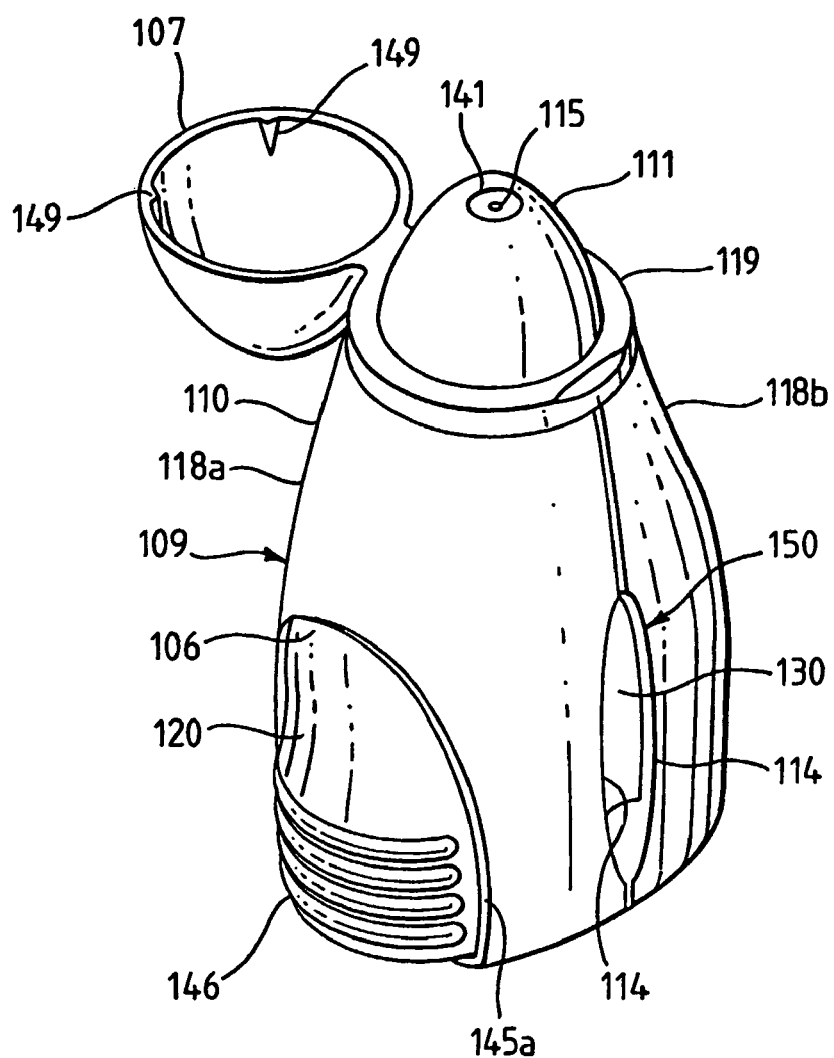
FIG. 7 is a view similar to that of FIG. 6 but viewed from a front left hand corner showing the fluid dispensing device in a ready for use state with the protective end cap removed.
Figure 7A:
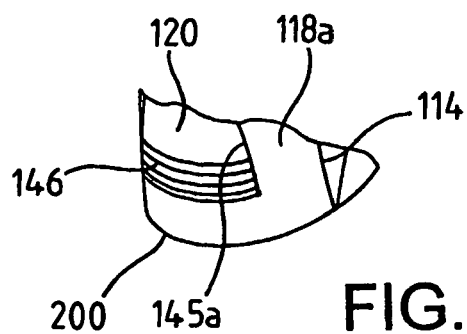
FIG. 7a is a scrap view of part of the fluid dispensing device shown in FIG. 7 showing a modification to the device.
Figure 8:
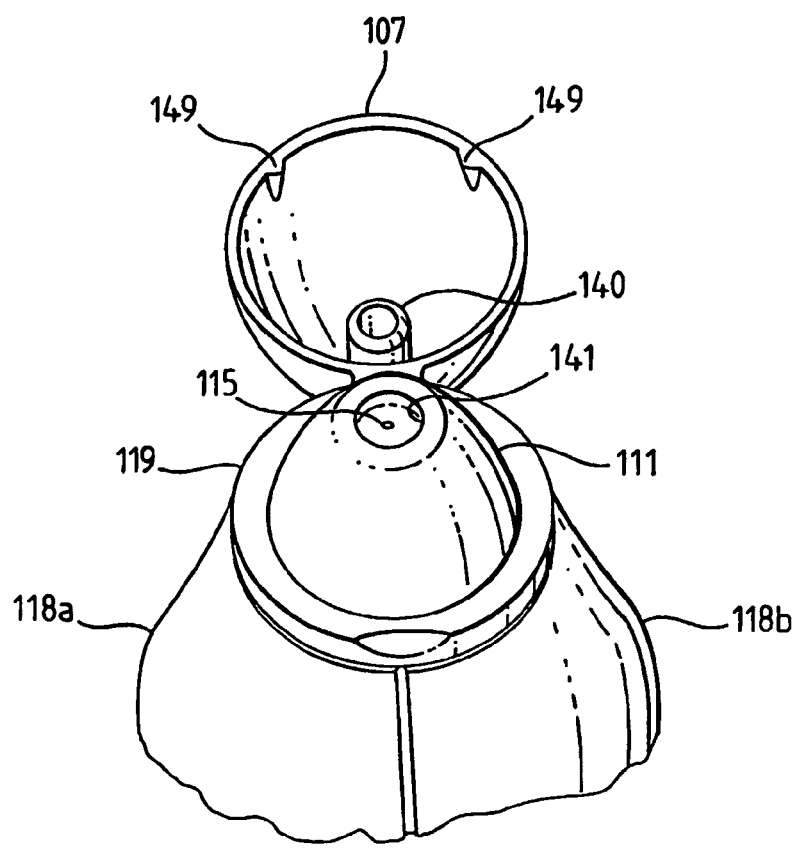
FIG. 8 is an enlarged pictorial view from the front and above of a top portion of the fluid dispensing device shown in FIG. 7.

As is shown in FIG. 7a the fluid dispensing device includes a means to prevent inadvertent movement of the two levers when not in use. The means is a portion of each cover member 118a, 118b which overlies an end portion of each lever 120, 121. More specifically, each of the cover shells 118a, 118b extends around the base portion of the cover to provide an overlying shield 200. The shields 200 act as a means to prevent inadvertent movement of the two levers 120, 121.

The advantage of this construction is that accidental operation of the dispensing device when it is carried in a bag or pocket or generally is less likely to occur because the bottom portions of the levers 120, 121 are covered and specific finger pressure has to be applied. It will be appreciated that a physical locking mechanism could also or alternatively be provided to prevent accidental movement of the two levers 120, 121.

The body member 106 is engaged with the annular ring 119 to fasten the cover member 110 to the body member 106. The body member 106 has a cylindrical portion for engagement with the annular ring 119.

Two detents 143 are formed on the cylindrical portion and two legs 144 are connected near to one end of the cylindrical portion. The detents 143 are used to trap the annular ring 119 against the legs 144 and thereby form a snap connection used to fasten the body member 106 to the cover member 110. It will be appreciated that other forms of snap fastening means could be provided.

Each of the levers 120, 121 is pivotally connected to the body member 106 by a living hinge 126, 127. The living hinges 126, 127 are formed at the juncture of the levers 120, 121 with the legs 144.

However, it will be appreciated that the levers could alternatively be pivotally connected to the cover member by a living hinge and that in either case the invention is not limited to the use of a living hinge other hinge mechanisms could be used.

The discharge outlet from the pump 129 is in the form of a tubular delivery tube (not shown) and a tubular guide in the form of an outlet tube (not shown) is formed within the nozzle 111 to align and locate the delivery tube correctly with respect to the nozzle 111.

An annular abutment is formed at the end of the outlet tube. The annular abutment defines the entry to an orifice 115 through which fluid can flow in use and is arranged for abutment with an end of the delivery tube.

The fluid discharge device 108 has a longitudinal axis Z-Z and each of the levers 120, 121 has an abutment surface 122 (only one of which is visible in the Figures) arranged at an angle to the longitudinal axis Z-Z of the fluid discharge device 108 for abutment against a base portion 135 of the container so as to convert a force applied to the levers 120, 121 substantially transversely to the longitudinal axis Z-Z of the fluid discharge device 108 into a force along the longitudinal axis Z-Z of the fluid discharge device 108.

This arrangement allows a standard fluid discharge device to be used without modification.

The nozzle 111 has a longitudinal axis P-P and the longitudinal axis Z-Z of the fluid discharge device 108 is aligned with the longitudinal axis P-P of the nozzle 111. This has the advantage that when the pump 129 is actuated the force applied to the tubular delivery tube is along the axis of the tubular delivery tube and no bending or deflection of the delivery tube will occur due to the applied force.

At least part of the surface of the base portion 135 of the container 130 is inclined at an angle with respect to the longitudinal axis Z-Z of the fluid discharge device 108 so as to form an inclined surface, the or each inclined surface being arranged to be acted upon by the levers 120, 121 so as to convert a force applied to the levers 120, 121 substantially transversely to the longitudinal axis Z-Z of the fluid discharge device 108 into a force along the longitudinal axis Z-Z of the fluid discharge device 108.

Although in the disclosed embodiment both the levers and the container have surfaces inclined to the longitudinal axis of the fluid discharge device this need not be the case. Only the container or the levers need have an inclined surface or some other arrangement to apply the force from the levers to the container could be used.

In accordance with this embodiment the base portion 135 of the container has a conical inclined surface 138 arranged for co-operation with the levers 120, 121.

However, it will be appreciated that the inclined surface of the base portion of the container could be a frusto-conical or part spherical surface or could be comprised of two separate inclined surfaces each for co-operation with a respective one of the levers.

The inclined surface 138 is arranged to co-operate with both abutment surfaces 122 of the levers 120, 121.

The abutment surfaces 122 are both formed by one surface of triangular web 124 formed as part of each lever 120, 121. At the end of each abutment surface there is formed a pre-loading means in the form of a ridge 170 (only one of which is shown). The purpose of this ridge 170 is to introduce a pre-load effect into the mechanism which has to be overcome by applying more than a pre-determined load to allow the fluid to be dispensed.

In the ready for use position this lies against a side of the container 130 at the juncture of the side of the container 130 with the base portion 135. The purpose of this ridge is to prevent the levers 120, 121 from moving the container 130 until more than a pre-determined load has been applied to the levers 120, 121. Once this pre-determined load is exceeded the pressure being applied to the levers is such that the container 130 is very rapidly moved towards the nozzle 111. This prevents the levers 120, 121 being slowly squeezed together which will not produce a uniform spray and if done very slowly will merely cause the fluid to dribble out of the nozzle 111. However, it will be appreciated that many alternative mechanisms could be employed to produce this pre-load effect. For example the angle of contact could be such that until the levers have been displaced or deflected the force is not efficiently transferred or the levers could be prevented from movement by some form of detent mechanism or the pump itself could be provided with a mechanism that needs to be overcome.

The fluid discharge device 108 is in most respects conventional and will only be described briefly herein.

The fluid discharge device 108 has a hollow container 130 defining a reservoir containing several doses of the fluid to be dispensed and a compression pump 129 attached to one end of the container 130.

The container 130 as shown is made from glass however it will be appreciated that it could be made from other translucent or transparent materials such as plastic. The pump 129 includes a plunger (not shown) slidingly engaged within a pump casing 134 which defines a chamber (not shown) sized to accommodate a single dose of fluid. The plunger is attached to the tubular delivery tube which is arranged to extend from one end of the pump 129 for co-operation with the outlet tube of the dispensing nozzle 111. The plunger includes a piston (not shown) slidably supported in the chamber formed in the pump casing 134.

The fluid is discharged through a discharge channel defined by the tubular delivery tube into the orifice 115 of the dispensing nozzle 111.

The size of chamber is such that it accommodates a single dose of fluid, the diameter of the chamber and piston combined with the stroke of the plunger being such that a full stroke of the plunger in the chamber will produce a change in volume equal to a single dose of fluid.

The pump casing 134 is connected to the container 130 such that when the piston is moved by an internal return spring (not shown) into a start position a new dose of fluid is drawn into the cylinder via the suction inlet in the form of a pick-up tube from the container 130 ready for discharge.

The conical form of the base portion 135 of the container 130 is particularly advantageous in that it allows the pick up tube to collect more fluid, without special orientation of the container, than if a flat bottomed container is used.

Assembly and operation of the fluid dispensing device is as follows.

Figure 9:
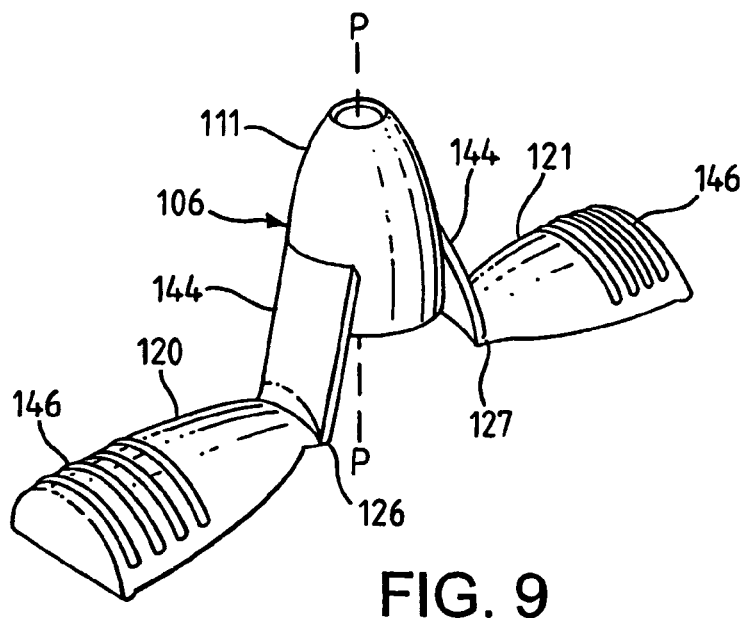
FIG. 9 is a pictorial view of a body member forming part of the fluid dispensing device shown in FIG. 7 in a pre-assembled condition.
Figure 10:
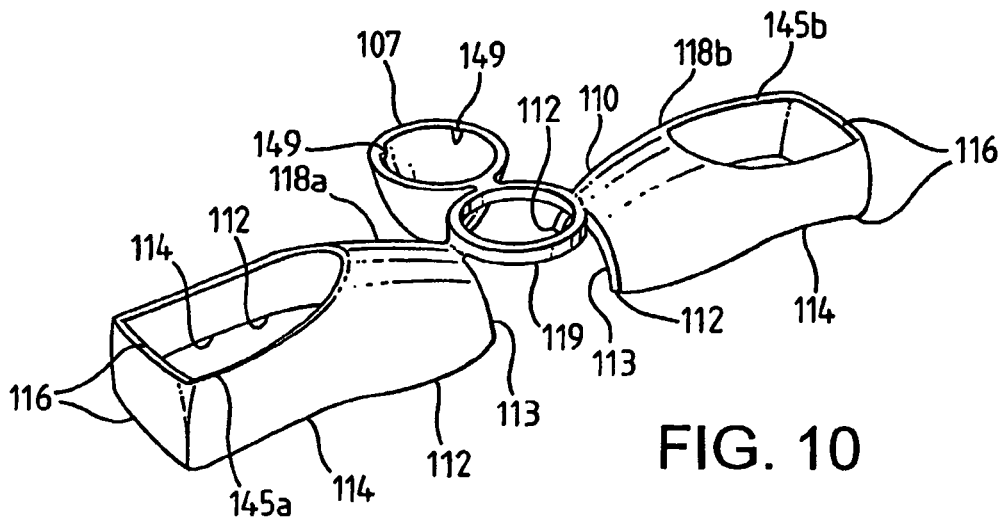
FIG. 10 is a pictorial view of a cover member forming part of the fluid dispensing device shown in FIG. 7 in a pre-assembled condition.

The first stage of assembly is to position the levers 120, 121 in the position shown in FIG. 9 and then insert the fluid discharge device 108 into the body member 106.

This is done by engaging the pump casing 134 with a cylindrical bore in the cylindrical portion of the body member 106 and engaging the delivery tube with the outlet tube such that an end of the delivery tube is in abutment with the annular abutment in the outlet tube. The engagement of the pump casing 134 with the cylindrical portion of the body member 106 is such that the pump casing 134 is able to slide in the cylindrical bore when a force is applied to the container 130 but is gripped sufficiently to hold the fluid discharge device 108 in position.

Figure 11:
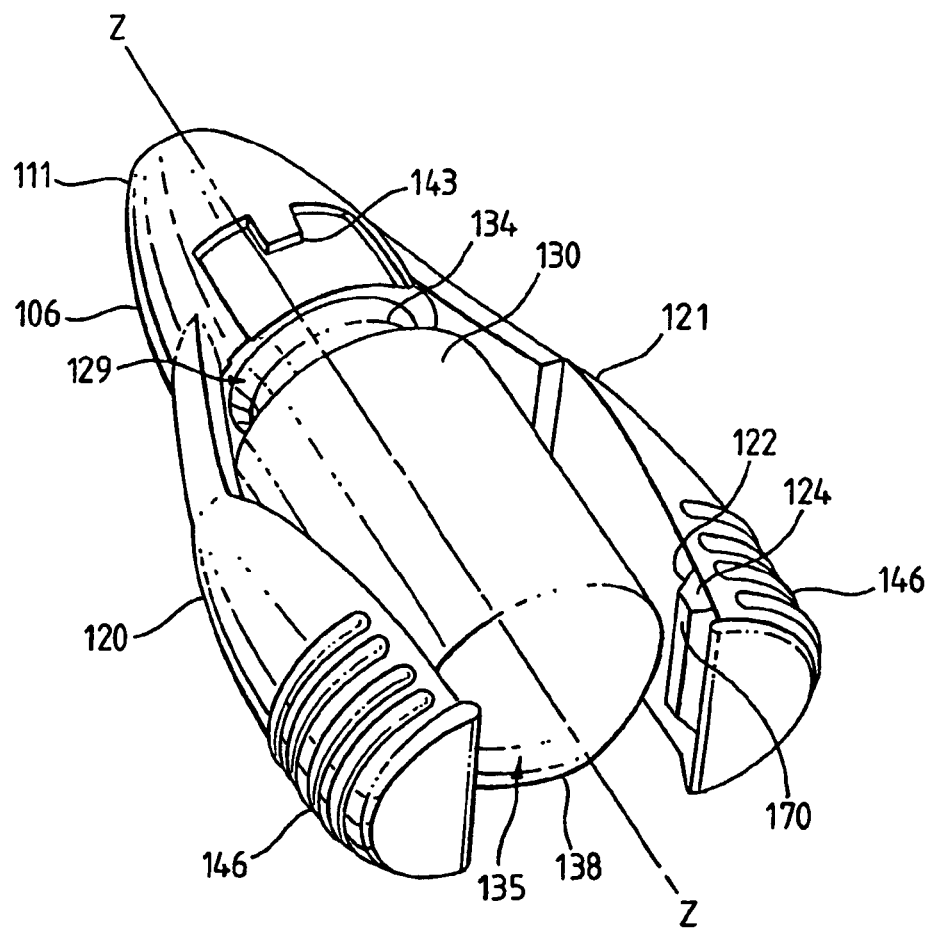
FIG. 11 is a pictorial view of the body member shown in FIG. 9 in a partly assembled condition in which a fluid discharge device according to the second aspect of the invention has been inserted.

FIG. 11 shows the fluid dispensing device 105 in a partly assembled state after this initial assembly operation in which the fluid discharge device 108 has been inserted into the body member 106. The two levers 120, 121 have been folded down from the position shown in FIG. 9 into a ready for use position such that end portions of the abutment surfaces 122 and in particular the ridges 170 are positioned adjacent to a side wall of the container and near to the inclined conical surface 138 of the container 130.

To complete the assembly of the fluid dispensing device 105 the cylindrical portion of the body member 106 is inserted into the annular ring 119 and the two parts are snapped together. The two cover shells 118a and 118b are then folded down from the position shown in FIG. 10 into the position shown in FIG. 6.

Figure 6:
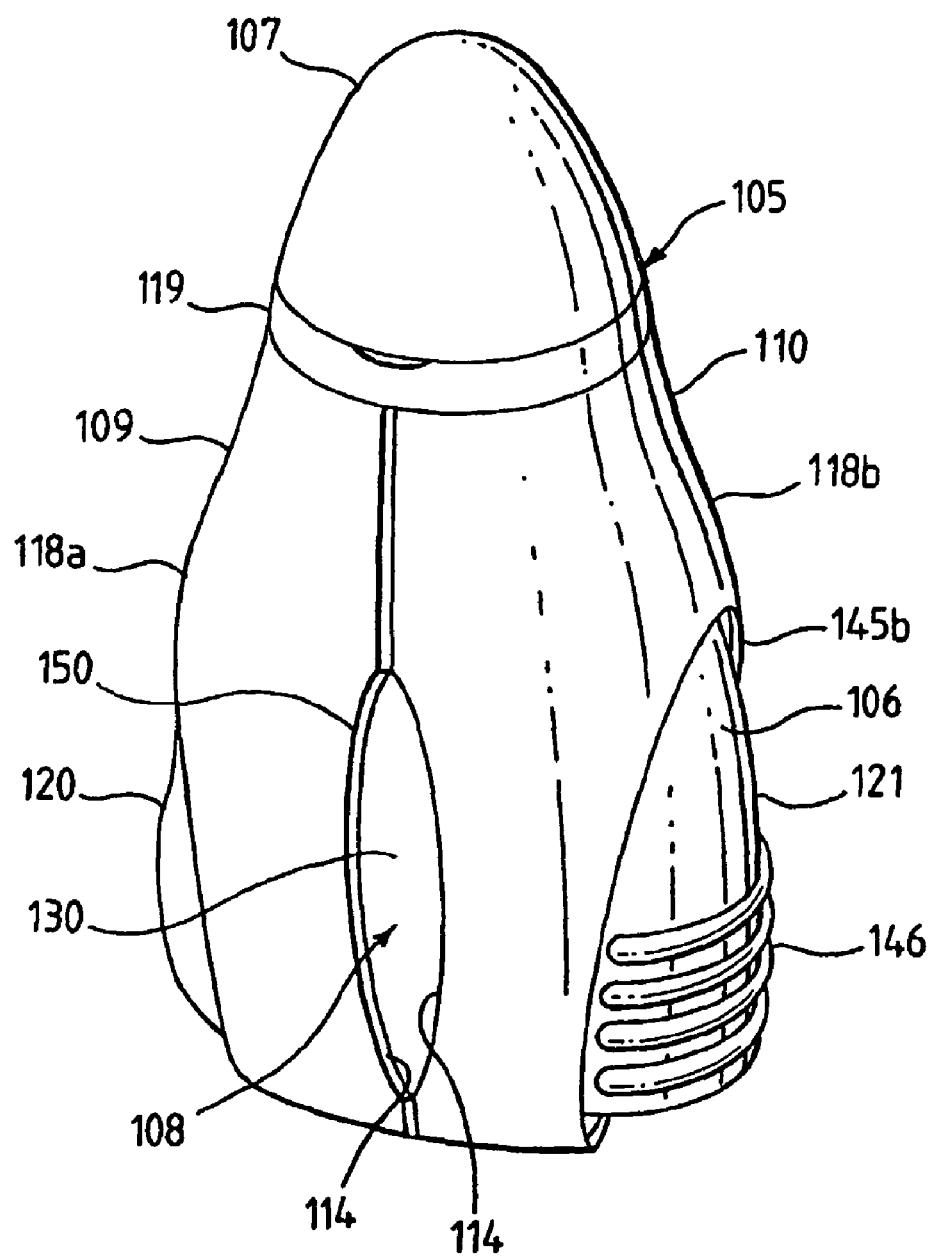
FIG. 6 is a pictorial representation as viewed from a front right hand corner of a second embodiment of a fluid dispensing device according to the invention in a stored state with a protective end cap in place.

The abutting transverse edges 116 of the two cover shells 118a and 118b include complementary detents (not shown) such that when the cover shells 118a, 118b are pushed together the detents snap together to hold them in the position shown in FIGS. 6 and 7. As an additional measure an adhesive backed label (not shown) can be applied across the joint between the two cover shells 118a and 118b on the base on the assembled fluid dispensing device 105 to prevent the cover shells 118a, 118b from accidentally snapping open but more importantly to provide an indication that the fluid dispensing device 105 has not been tampered with.

To use the fluid dispensing device 105 a user first has to remove the protective cap 107 (as shown in FIG. 7) and then the user must grasp the fluid dispensing device 105 by the two levers 120, 121 and in particular by the two ribbed finger grips 146.

Provided that only a light pressure is applied to the levers 120, 121 no fluid will be discharged and the user is able to manoeuvre the dispensing nozzle 111 of the fluid dispensing device 105 into a body orifice such as a nasal cavity into which fluid is required to be dispensed. This is because of the presence of the pre-load mechanism 170.

If the user then squeezes the two levers 120, 121 together with increasing force the pre-determined load will eventually be exceeded and the interaction of the abutment surfaces 122 upon the inclined conical surface 138 will then cause the container 130 to be moved rapidly towards the nozzle 111.

However, because of the abutment between the end of the delivery tube and the annular abutment movement of the delivery tube in the same direction is prevented and therefore the delivery tube acts so as to push the plunger into the pump casing 134 thereby moving the piston of the pump in the cylinder. This causes fluid to be expelled from the cylinder into the delivery tube and then into the orifice 115 from where it is expelled as a fine spray into the body orifice.

Upon releasing the pressure applied to the levers 120, 121 the delivery tube is urged out of the pump casing by the internal return spring and causes fluid to be drawn up the pick-up tube to re-fill the cylinder.

The actuating procedure can then be repeated until all of the fluid in the container has been used. However, only one or two doses of fluid are normally administered at a time.

When the container 130 is empty a new fluid discharge device 108 is loaded into the body member 106 thereby restoring the fluid dispensing device 105 into a useable condition.

It will be appreciated that because the action of squeezing the two levers together requires the application of equal and opposite forces to be applied to the two levers the nozzle is less likely to move around or be displaced when the dose is supplied and the squeezing action tends to produce a smooth controllable delivery of fluid.

It will be further appreciated that the force supplied to both levers is directed into the container and so the fluid dispensing device makes a more efficient use of the applied force compared to a single lever arrangement in which some of the force is lost in resisting the applied force with no increase in applied force to the container.

It is envisaged that the fluid dispensing device could be sold as two separate items. A fluid discharge device could be sold for fitment into a housing assembly and a housing assembly could be sold into which a fluid discharge device could be fitted.

It will be understood that the present disclosure is for the purpose of illustration only and the invention extends to modifications, variations and improvements thereto.

For example although the two embodiments describe in detail an arrangement in which the two levers act upon a base portion of the container and push it towards the nozzle it would also possible to arrange for the two leavers to pull the container towards the nozzle. The invention is not therefore to be construed as being limited solely to a device that pushes the container towards the nozzle.

Administration of medicament may be indicated for the treatment of mild, moderate or severe acute or chronic symptoms or for prophylactic treatment. It will be appreciated that the precise dose administered will depend on the age and condition of the patient, the particular medicament used and the frequency of administration and will ultimately be at the discretion of the attendant physician. When combinations of medicaments are employed the dose of each component of the combination will in general be that employed for each component when used alone.

Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (eg as the sodium salt), ketotifen or nedocromil (eg as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (eg as the dipropionate ester), fluticasone (eg as the propionate ester), flunisolide, budesonide, rofleponide, mometasone (eg as the furoate ester), ciclesonide, triamcinolone (eg as the acetonide), 6α, 9α-difluoro-11β-hydroxy-16α-methyl-3-oxo-17α-propionyloxy-androsta-1,4-diene-17β-carbothioic acid S-(2-oxo-tetrahydro-furan-3-yl)ester or 6α, 9α-Difluoro-17α-[(2-furanylcarbonyl)oxy]-11β-hydroxy-16α-methyl-3-oxo-androsta-1,4-diene-17β-carbothioic acid S-fluoromethyl ester; antitussives, e.g., noscapine; bronchodilators, e.g., albuterol (eg as free base or sulphate), salmeterol (eg as xinafoate), ephedrine, adrenaline, fenoterol (eg as hydrobromide), formoterol (eg as fumarate), isoprenaline, metaproterenol, phenylephrine, phenylpropanolamine, pirbuterol (eg as acetate), reproterol (eg as hydrochloride), rimiterol, terbutaline (eg as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; PDE4 inhibitors eg cilomilast or roflumilast; leukotriene antagonists eg montelukast, pranlukast and zafirlukast; [adenosine 2a agonists, eg 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate)]*; [α4 integrin inhibitors eg (2S)-3-[4-({[4-(aminocarbonyl)-1-piperidinyl]carbonyl}oxy)phenyl]-2-[((2S)-4-methyl-2-{[2-(2-methylphenoxy) acetyl]amino}pentanoyl)amino]propanoic acid (e.g as free acid or potassium salt)]*, diuretics, e.g., amiloride; anticholinergics, e.g., ipratropium (eg as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagons. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament and/or to minimise the solubility of the medicament in the propellant.

Preferably, the medicament is an anti-inflammatory compound for the treatment of inflammatory disorders or diseases such as asthma and rhinitis.

In one aspect, the medicament is a glucocorticoid compound, which has anti-inflammatory properties. One suitable glucocorticoid compound has the chemical name: 6α, 9α-Difluoro-17α-(1-oxopropoxy)-11β-hydroxy-16α-methyl-3-oxo-androsta-1,4-diene-17β-carbothioic acid S-fluoromethyl ester (fluticasone propionate). Another suitable glucocorticoid compound has the chemical name: 6α, 9α-difluoro-17α-[(2-furanylcarbonyl)oxy]-11β-hydroxy-16α-methyl-3-oxo-androsta-1,4-diene-17β-carbothioic acid S-fluoromethyl ester. A further suitable glucocorticoid compound has the chemical name: 6α, 9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester.

Other suitable anti-inflammatory compounds include NSAIDs e.g. PDE4 inhibitors, leukotriene antagonists, iNOS inhibitors, tryptase and elastase inhibitors, beta-2 integrin antagonists and adenosine 2a agonists.

The medicament is formulated as any suitable fluid formulation, particularly a solution (e.g. aqueous) formulation or a suspension formulation, optionally containing other pharmaceutically acceptable additive components.

Suitable formulations (e.g. solution or suspension) may be stabilised (e.g. using hydrochloric acid or sodium hydroxide) by appropriate selection of pH. Typically, the pH will be adjusted to between 4.5 and 7.5, preferably between 5.0 and 7.0, especially around 6 to 6.5.

Suitable formulations (e.g. solution or suspension) may comprise one or more excipients. By the term "excipient", herein, is meant substantially inert materials that are nontoxic and do not interact with other components of a composition in a deleterious manner including, but not limited to, pharmaceutical grades of carbohydrates, organic and inorganic salts, polymers, amino acids, phospholipids, wetting agents, emulsifiers, surfactants, poloxamers, pluronics, and ion exchange resins, and combinations thereof.

Suitable carbohydrates include monosaccharides include fructose; disaccharides, such as, but not limited to lactose, and combinations and derivatives thereof; polysaccharides, such as, but not limited to, cellulose and combinations and derivatives thereof; oligosaccharides, such as, but not limited to, dextrins, and combinations and derivatives thereof; polyols, such as but not limited to sorbitol, and combinations and derivatives thereof.

Suitable organic and inorganic salts include sodium or calcium phosphates, magnesium stearate, and combinations and derivatives thereof.

Suitable polymers include natural biodegradable protein polymers, including, but not limited to, gelatin and combinations and derivatives thereof; natural biodegradable polysaccharide polymers, including, but not limited to, chitin and starch, crosslinked starch and combinations and derivatives thereof; semisynthetic biodegradable polymers, including, but not limited to, derivatives of chitosan; and synthetic biodegradable polymers, including, but not limited to, polyethylene glycols (PEG), polylactic acid (PLA), synthetic polymers including but not limited to polyvinyl alcohol and combinations and derivatives thereof;

Suitable amino acids include non-polar amino acids, such as leucine and combinations and derivatives thereof. Suitable phospholipids include lecithins and combinations and derivatives thereof.

Suitable wetting agents, surfactants and/or emulsifiers include gum acacia, cholesterol, fatty acids including combinations and derivatives thereof. Suitable poloxamers and/or Pluronics include poloxamer 188, Pluronic® F-108, and combinations and derivations thereof. Suitable ion exchange resins include amberlite IR120 and combinations and derivatives thereof;

Suitable solution formulations may comprise a solubilising agent such as a surfactant. Suitable surfactants include α-[4-(1,1,3,3-tetramethylbutyl)phenyl]-ω-hydroxypoly(oxy-1,2-ethanediyl) polymers including those of the Triton series e.g. Triton X-100, Triton X-114 and Triton X-305 in which the X number is broadly indicative of the average number of ethoxy repeating units in the polymer (typically around 7-70, particularly around 7-30 especially around 7-10) and 4-(1,1,3,3-tetramethylbutyl)phenol polymers with formaldehyde and oxirane such as those having a relative molecular weight of 3500-5000 especially 4000-4700, particularly Tyloxapol. The surfactant is typically employed in a concentration of around 0.5-10%, preferably around 2-5% w/w based on weight of formulation.

Suitable solution formulations may also comprise hydroxyl containing organic co-solvating agents include glycols such as polyethylene glycols (eg PEG 200) and propylene glycol; sugars such as dextrose; and ethanol. Dextrose and polyethylene glycol (eg PEG 200) are preferred, particularly dextrose. Propylene glycol is preferably used in an amount of no more than 20%, especially no more than 10% and is most preferably avoided altogether. Ethanol is preferably avoided. The hydroxyl containing organic co-solvating agents are typically employed at a concentration of 0.1-20% e.g. 0.5-10%, e.g. around 1-5% w/w based on weight of formulation.

Suitable solution formulations may also comprise solubilising agents such as polysorbate, glycerine, benzyl alcohol, polyoxyethylene castor oils derivatives, polyethylene glycol and polyoxyethylene alkyl ethers (e.g. Cremophors, Brij).

Suitable solution formulations may also comprise one or more of the following components: viscosity enhancing agents; preservatives; and isotonicity adjusting agents.

Suitable viscosity enhancing agents include carboxymethylcellulose, veegum, tragacanth, bentonite, hydroxypropylmethylcellulose, hydroxypropylcellulose, hydroxyethylcellulose, poloxamers (eg. poloxamer 407), polyethylene glycols, alginates xanthym gums, carageenans and carbopols.

Suitable preservatives include quaternary ammonium compounds (e.g. benzalkonium chloride, benzethonium chloride, cetrimide and cetylpyridinium chloride), mercurial agents (e.g. phenylmercuric nitrate, phenylmercuric acetate and thimerosal), alcoholic agents (e.g. chlorobutanol, phenylethyl alcohol and benzyl alcohol), antibacterial esters (e.g. esters of para-hydroxybenzoic acid), chelating agents such as disodium edetate (EDTA) and other anti-microbial agents such as chlorhexidine, chlorocresol, sorbic acid and its salts and polymyxin.

Suitable isotonicity adjusting agents act such as to achieve isotonicity with body fluids (e.g. fluids of the nasal cavity), resulting in reduced levels of irritancy associated with many nasal formulations. Examples of suitable isotonicity adjusting agents are sodium chloride, dextrose and calcium chloride.

Suitable suspension formulations comprise an aqueous suspension of particulate medicament and optionally suspending agents, preservatives, wetting agents or isotonicity adjusting agents.

The particulate medicament suitably has a mass mean diameter (MMD) of less than 20 µm, preferably between 0.5-10 µm, especially between 1-5 µm. If particle size reduction is necessary, this may be achieved by techniques such as micronisation and/or microfluidisation.

Suitable suspending agents include carboxymethylcellulose, veegum, tragacanth, bentonite, methylcellulose and polyethylene glycols.

Suitable wetting agents function to wet the particles of medicament to facilitate dispersion thereof in the aqueous phase of the composition. Examples of wetting agents that can be used are fatty alcohols, esters and ethers. Preferably, the wetting agent is a hydrophilic, non-ionic surfactant, most preferably polyoxyethylene (20) sorbitan monooleate (supplied as the branded product Polysorbate 80).

Suitable preservatives and isotonicity adjusting agents are as described above in relation to solution formulations.

The dispensing device herein is suitable for dispensing fluid medicament formulations for the treatment of inflammatory and/or allergic conditions of the nasal passages such as rhinitis e.g. seasonal and perennial rhinitis as well as other local inflammatory conditions such as asthma, COPD and dermatitis.

A suitable dosing regime would be for the patient to inhale slowly through the nose subsequent to the nasal cavity being cleared. During inhalation the formulation would be applied to one nostril while the other is manually compressed. This procedure would then be repeated for the other nostril. Typically, one or two inhalations per nostril would be administered by the above procedure up to three times each day, ideally once daily. Each dose, for example, may deliver 5 µg, 50 µg, 100 µg, 200 µg or 250 µg of active medicament. The precise dosage is either known or readily ascertainable by those skilled in the art.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims.

The invention claimed is:

1. A fluid dispensing device for spraying a fluid into a body cavity comprising a housing, a nozzle for insertion into a body cavity, a fluid discharge device moveably housed within the housing, the fluid discharge device comprising a container for storing the fluid to be dispensed and a compression pump having a suction inlet located within the container and a discharge outlet for transferring fluid from the pump to the nozzle and finger operable means to apply a force to the container to move the container towards the nozzle so as to actuate the pump wherein the finger operable means comprises of two opposing levers each of which is pivotally connected to part of the housing and is arranged to act upon the container so as to urge the container towards the nozzle when the two levers are squeezed together by a user;
in which the fluid discharge device has a longitudinal axis and at least part of the surface of a base portion of the container is inclined at an angle with respect to the longitudinal axis of the fluid discharge device so as to form an inclined surface, the or each inclined surface being arranged to be acted upon by the levers so as to convert a force applied to the levers substantially transversely to the longitudinal axis of the fluid discharge device into a force along the longitudinal axis of the fluid discharge device.

2. A fluid dispensing device as claimed in claim 1 in which the fluid discharge device has a longitudinal axis and each of the levers has an abutment surface arranged at an angle to the longitudinal axis of the fluid discharge device for abutment against a base portion of the container so as to convert a force applied to the levers substantially transversely to the longitudinal axis of the fluid discharge device into a force along the longitudinal axis of the fluid discharge device.

3. A fluid dispensing device as claimed in claim 2 in which the nozzle has a longitudinal axis and the longitudinal axis of the fluid discharge device is aligned with the longitudinal axis of the nozzle.

4. A fluid dispensing device as claimed in claim 1 in which the inclined surface of the base portion of the container is a conical surface.

5. A fluid dispensing device as claimed in 1 in which the base portion of the container has two inclined surfaces each arranged for co-operation with a respective one of the levers.

6. A fluid dispensing device as claimed in claim 4 in which the container has two or more supports to allow the container to be stood up on the base portion.

7. A fluid dispensing device as claimed in claim 1 in which the housing and the nozzle are made as a single a plastic component.

8. A fluid dispensing device as claimed in claim 7 in which each of the levers is pivotally connected to part of the housing by a respective living hinge.

9. A fluid dispensing device as claimed in claim 7 in which the housing has a front wall, a rear wall and two opposing side walls and each of the levers is pivotally connected to a respective one of the two side walls by a living hinge.

10. A fluid dispensing device as claimed in claim 9 in which at least one of the front wall and the rear wall has an aperture therein to view the level of the fluid in the container.

11. A fluid dispensing device as claimed in 10 in which there are apertures in the front and rear walls to view the level of the fluid in the container.

12. A fluid dispensing device as claimed in claim 7 in which the discharge outlet from the pump is a tubular delivery tube and a tubular guide is formed within the nozzle to align and locate the delivery tube correctly with respect to the nozzle.

13. A fluid dispensing device as claimed in claim 1 in which the housing comprises of a plastic cover member and a plastic body member.

14. A fluid dispensing device as claimed in claim 13 in which the nozzle is formed as an integral part of the body member.

15. A fluid dispensing device as claimed in claim 14 in which the body member is fastened within the cover member so that the nozzle projects from one end of the cover member.

16. A fluid dispensing device as claimed in claim 14 in which each of the levers is pivotally connected to the body member by a living hinge.

17. A fluid dispensing device as claimed in claim 13 in which the discharge outlet from the pump is a tubular delivery tube and a tubular guide is formed within the body member to align and locate the delivery tube correctly with respect to the nozzle.

18. A fluid dispensing device as claimed in claim 13 in which the cover member comprises of two cover shells joined together at one end by an annular ring.

19. A fluid dispensing means as claimed in claim 17 in which the body member is engaged with the annular ring to fasten the cover member to the body member.

20. A fluid dispensing device as claimed in claim 18 in which each of the cover shells has an aperture formed therein from which, in use, a part of a respective one of the levers projects.

21. A fluid dispensing device as claimed in claim 20 in which the part of each lever which projects from the aperture is a ribbed finger grip.

22. A fluid dispensing device as claimed in claim 18 in which at least one longitudinal edge of each cover shell has a recess formed therein and the recesses co-operate to define a window through which the level of the fluid in the container can be checked.

23. A fluid dispensing device as claimed in claim 22 in which both longitudinal edges of each cover shell have a recess formed therein and the recesses co-operate to define two windows on opposite sides of the housing through which the level of the fluid in the container can be checked.

24. A fluid dispensing device as claimed in claim 18 in which a protective end cap for the nozzle is connected to the annular ring.

25. A fluid dispensing device as claimed in claim 24 in which the end cap, the annular ring and the two cover shells are made as a one piece plastic component.

26. A fluid dispensing device as claimed in claim 1 wherein said container contains a volume of fluid medicament formulation.

27. A device as claimed in claim 26, wherein said fluid medicament formulation is in the form of a solution formulation.

28. A device as claimed in claim 26, wherein said fluid medicament formulation is in the form of a suspension formulation.

29. A device as claimed in claim 26, wherein the fluid medicament formulation comprises an anti-inflammatory medicament compound.

30. A device as claimed in claim 29, wherein said medicament compound is a glucocorticoid compound.

31. A device as claimed in claim 30, wherein said glucocorticoid compound is selected from the group consisting of $6\alpha$, $9\alpha$-Difluoro-$17\alpha$-(1-oxopropoxy)-$11\beta$-hydroxy-$16\alpha$-methyl-3-oxo-androsta-1,4-diene-$17\beta$-carbothioic acid S-fluoromethyl ester; $6\alpha$, $9\alpha$-difluoro-$17\alpha$-[(2-furanylcarbonyl)oxy]-$11\beta$-hydroxy-$16\alpha$-methyl-3-oxo-androsta-1,4-diene-$17\beta$-carbothioic acid S-fluoromethyl ester; and $6\alpha,9\alpha$Difluoro-$11\beta$-hydroxy-$16\alpha$-methyl-$17\alpha$-[(4-methyl-1,3-thiazole-5-carbonyl)oxy]-3-oxo-androsta-1,4-diene-$17\beta$-carbothioic acid S-fluoromethyl ester.

32. A device as claimed in claim 29, wherein said medicament compound is selected from the group consisting of PDE4 inhibitors, leukotriene antagonists, iNOS inhibitors, tryptase inhibitors, elastase inhibitors, beta-2 integrin antagonists and adenosine 2a agonists.

33. A fluid discharge device for use in a fluid dispensing device as claimed in claim 1 wherein the fluid discharging device comprises of a container for storing a fluid to be dispensed and a compression pump attached to one end of the container, the pump having a suction inlet located within the container and a discharge outlet for transferring, in use fluid from the pump to a nozzle wherein the fluid discharge device has a longitudinal axis and the container has a base portion at least part of which is inclined at an angle with respect to the longitudinal axis of the fluid discharge device.

34. A fluid discharge device as claimed in claim 33 in which the inclined surface of the base portion of the container is a conical surface.

35. A fluid discharge device as claimed in claim 33 in which the base portion of the container has two opposing inclined surfaces.

36. A fluid dispensing device as claimed in claim 33 in which the container has two or more supports to allow the container to be stood up on the base portion.

37. A fluid dispensing device comprising a housing assembly for a fluid discharge device, and a fluid discharge device moveably housed within the housing assembly, the housing assembly comprising a housing for moveably supporting the discharge device, a nozzle extending from the housing for insertion into a body cavity and finger operable means to apply, in use, a force to the fluid discharging device wherein the finger operable means comprises of two opposing levers to apply, in use, a force to the fluid discharging device so as to actuate the fluid discharge device and supply fluid to the nozzle;

in which the housing comprises of a plastic cover member and a plastic body member and the nozzle is formed as an integral part of the body member;

in which each of the levers is pivotally connected to the body member by a living hinge;

in which in which the fluid discharge device has a longitudinal axis and a base portion; and at least part of the surface of the base portion of the fluid discharge device is inclined at an angle with respect to the longitudinal axis of the fluid discharge device so as to form an inclined surface, the or each inclined surface being arranged to be acted upon by the levers so as to convert a force applied to the levers substantially transversely to the longitudinal axis of the fluid discharge device into a force along the longitudinal axis of the fluid discharge device.

38. An assembly as claimed in claim 37 in which the body member is fastened within the cover member so that the nozzle projects from one end of the cover member.

39. An assembly as claimed in claim 37 in which a tubular guide is formed within the body member to align and locate, in use, a delivery tube of the fluid discharge device correctly with respect to the nozzle.

40. An assembly as claimed in claim 37 in which the cover member comprises of two cover shells joined together at one end by an annular ring.

41. An assembly as claimed in claim 40 in which the body member is engaged with the annular ring to fasten the cover member to the body member.

42. An assembly as claimed in claim 40 in which each of the cover shells has an aperture formed therein from which, in use, a part of a respective one of the levers projects.

43. An assembly as claimed in claim 42 in which the part of each lever which projects from the aperture is a ribbed finger grip.

44. An assembly as claimed in claim 40 in which at least one longitudinal edge of each cover shell has a recess formed therein and the recesses co-operate to define a window through which the level of the fluid in the container can be checked.

45. An assembly as claimed in claim 44 in which both longitudinal edges of each cover shell have a recess formed therein and the recesses co-operate to define two windows on opposite sides of the housing through which the level of the fluid in the container can be checked.

46. An assembly as claimed in claim 40 in which a protective end cap for the nozzle is connected to the annular ring.

47. An assembly as claimed in claim 46 in which the end cap, the annular ring and the two cover shells are made as a one piece plastic component.

48. An assembly as claimed in claim 37 in which each of the levers has an inclined abutment surface for abutment, in use, against the fluid discharge device so as to convert a force applied to the levers substantially transversely to a longitudinal axis of the fluid discharge device into a force along the longitudinal axis of the fluid discharge device.

* * * * *